United States Patent
Alley et al.

(10) Patent No.: US 9,168,142 B2
(45) Date of Patent: Oct. 27, 2015

(54) POROUS SURFACE LAYERS WITH INCREASED SURFACE ROUGHNESS AND IMPLANTS INCORPORATING THE SAME

(71) Applicant: Smith & Nephew, Inc., Memphis, TN (US)

(72) Inventors: Carie Fincher Alley, Memphis, TN (US); Laura J. Gilmour, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/163,200

(22) Filed: Jan. 24, 2014

(65) Prior Publication Data

US 2014/0138010 A1    May 22, 2014

Related U.S. Application Data

(62) Division of application No. 13/126,737, filed as application No. PCT/US2009/061881 on Oct. 23, 2009, now abandoned.

(60) Provisional application No. 61/109,395, filed on Oct. 29, 2008.

(51) Int. Cl.
| | |
|---|---|
| *A61F 2/34* | (2006.01) |
| *B05D 1/12* | (2006.01) |
| *A61F 2/30* | (2006.01) |
| *A61L 27/56* | (2006.01) |
| *A61L 27/30* | (2006.01) |

(Continued)

(52) U.S. Cl.
CPC .............. *A61F 2/3094* (2013.01); *A61L 27/56* (2013.01); *A61F 2/389* (2013.01); *A61F 2/3859* (2013.01); *A61F 2/44* (2013.01); *A61F 2002/3092* (2013.01); *A61F 2002/30968* (2013.01); *A61F 2310/00029* (2013.01); *A61F 2310/00089* (2013.01); *A61F 2310/00131* (2013.01); *A61L 27/306* (2013.01); *A61L 2400/18* (2013.01); *Y10T 156/10* (2015.01)

(58) Field of Classification Search
CPC ..... A61F 2/30767; B05D 1/12; A61L 21/306; A61L 27/56
USPC .............................. 427/2.24–2.27, 180, 2.26
See application file for complete search history.

(56) References Cited

U.S. PATENT DOCUMENTS

| | | | | |
|---|---|---|---|---|
| 4,542,539 A | * | 9/1985 | Rowe et al. | 623/23.57 |
| 5,368,881 A | * | 11/1994 | Kelman et al. | 427/2.26 |

(Continued)

OTHER PUBLICATIONS

International Search Report; International Patent Application No. PCT/US2009/061881; 2 pages, Nov. 3, 2014.

(Continued)

*Primary Examiner* — Cachet Sellman
(74) *Attorney, Agent, or Firm* — Taft Stettinius & Hollister LLP

(57) ABSTRACT

Systems and methods for providing tissue-interfacing surface layers with increased roughness can be attained by providing a metallic powder to a machined or previously machined tissue-interfacing surface of a porous foam structure. The metallic powder can have sizes and characteristics such that the porous structure can have an increased roughness at the tissue-interfacing machined surface while inhibiting the occlusion of the open pores in the porous metallic foam structure.

20 Claims, 12 Drawing Sheets

(51) Int. Cl.
  *A61F 2/38* (2006.01)
  *A61F 2/44* (2006.01)

(56) References Cited

U.S. PATENT DOCUMENTS

| | | | |
|---|---|---|---|
| 5,658,333 | A | 8/1997 | Kelman et al. |
| 6,544,472 | B1 * | 4/2003 | Compton et al. ............ 419/2 |
| 6,977,095 | B1 | 12/2005 | Marx et al. |
| 2003/0153981 | A1 * | 8/2003 | Wang et al. ............ 623/22.21 |
| 2006/0100716 | A1 | 5/2006 | Lerf |
| 2007/0081911 | A1 | 4/2007 | Charles |
| 2008/0199720 | A1 | 8/2008 | Liu |
| 2008/0300682 | A1 * | 12/2008 | Rivard et al. ............ 623/11.11 |
| 2010/0209666 | A1 * | 8/2010 | Rivard et al. ............ 428/148 |

OTHER PUBLICATIONS

Office Action; Chinese Patent Office; Chinese Application Serial No. 201410048576.5; Nov. 3, 2014; 7 pages.

* cited by examiner

POROUS SURFACE LAYERS WITH INCREASED SURFACE ROUGHNESS AND IMPLANTS INCORPORATING THE SAME

CROSS REFERENCE TO RELATED APPLICATIONS

This application is a divisional of U.S. patent application Ser. No. 13/126,737 filed Jun. 16, 2011, which is a U.S. National Phase filing of International Application No. PCT/US2009/061881 filed Oct. 23, 2009, which claims the benefit of U.S. Provisional Application No. 61/109,395 filed Oct. 29, 2008. The disclosure of this each of these prior applications is incorporated herein by reference in its entirety.

BACKGROUND OF THE INVENTION

1. Field of the Invention

The invention relates generally to surface layers with increased roughness, and more particularly to a method for increasing the roughness of a tissue-engaging outer surface of a porous structure without altering the pore size and porosity of the structure, and to medical implants incorporating said porous structure with increased surface roughness.

2. Description of the Related Art

Especially in the medical fields, the surface of an implant, device, or other implement can significantly affect function. For example, attempts have been made to improve bone implant stability by increasing the roughness of the implant. Other attempts have been made to improve bone implant stability by providing pores in the implant for bone ingrowth.

One method of achieving bone ingrowth in implants that contact bone (e.g., orthopedic implants) includes sintering metallic bead surfaces onto a substrate. Other methods of achieving bone ingrowth in implants includes using a reticulated foam porous coating fabricated from titanium that incorporates an electrical discharge machined (EDM) surface treatment, an EDM surface with axial grooves, an EDM surface with cross-hatching, or a photo-etched surface. Foam metal implants have been shown to achieve greater bone ingrowth than sintered bead implants. See, Urban, Robert M. et al., "Biomechanical and Histological Response to a Novel Foam Metal Porous Coating with Comparison of Two Methods for Measuring Bone Ingrowth," Transactions of the 54th Annual Meeting of the Orthopaedic Research Society, p. 1854, Mar. 2-5, 2008.

However, production of a porous metallic foam ingrowth structure (e.g., one created by applying fine metal powder particles to all surfaces of a porous structure) can require a secondary machining step to obtain the desired shape and dimensions (e.g., tolerances) of the machined metal foam structure. Such machining can cause a loss of roughness on the machined surfaces (e.g., tissue-engaging outer surfaces). The roughness can be maintained or recovered using textured molds during sintering to pressure-sinter particles to a substrate without sacrificing texture for porous bead-coated implants. Alternatively, the roughness for a metallic foam can be maintained or recovered using electrical discharge machining ("EDM"), creating a cross-hatch pattern and, upon implantation, gaps between the grooves in the coating and bone. These mechanisms have thus far proved unsatisfactory in increasing the roughness of machined tissue-engaging outer surfaces of a porous metallic foam ingrowth structure while maintaining the pore size and porosity of the structure.

Therefore, there is a need for an improved method for providing a porous metallic foam structure with improved bone ingrowth characteristics that avoids the drawbacks discussed above.

SUMMARY OF THE INVENTION

Embodiments of the invention are directed to increasing the surface roughness of a machined tissue-interfacing outer surface of a porous structure without altering the pore size or porosity of the porous structure.

In one embodiment a prosthetic implant comprises a machined reticulated porous structure. A powder comprising asymmetric particles can be disposed on a machined tissue-interfacing outer surface of the porous structure. The asymmetric particles can have a size of between about 30% and about 70% of the pore size in the porous structure so as to increase the surface roughness of the machined tissue-interfacing outer surface of the implant while substantially inhibiting the occlusion of the open pores of the porous structure and/or without substantially modifying the porosity of the porous structure. In one embodiment, the porous structure can be a porous metal body. Similarly, the powder can in one embodiment be a metallic powder. In other embodiments, the porous structure and powder can be of non-metallic materials.

In another embodiment a prosthetic implant comprises a previously machined reticulated porous structure to which one or more additional layers of powder have been applied to all surfaces of the previously machined reticulated porous structure. A powder comprising asymmetric particles can be disposed on a previously machined tissue-interfacing outer surface of the porous structure. The asymmetric particles can have a size of between about 30% and about 70% of the pore size in the porous structure so as to increase the surface roughness of the previously machined tissue-interfacing outer surface of the implant while substantially inhibiting the occlusion of the open pores of the porous structure and/or without substantially modifying the porosity of the porous structure In accordance with another embodiment, a prosthetic implant is provided comprising a machined reticulated porous construct applied to a solid surface. A powder comprising asymmetric powder particles can be adhered to a machined tissue-interfacing outer surface of the porous construct. The powder comprises a particle size configured to increase the surface roughness of the machined tissue-interfacing outer surface of the porous construct while substantially maintaining the open pores of the porous construct.

In accordance with still another embodiment, a prosthetic implant is provided comprising a previously machined reticulated porous construct to which one or more additional layers of powder have been applied to all surfaces and the construct applied to a solid surface. A powder comprising asymmetric powder particles can be adhered to a previously machined tissue-interfacing outer surface of the porous construct. The powder of asymmetric particles comprises a particle size configured to increase the surface roughness of the previously machined tissue-interfacing outer surface of the porous construct while substantially maintaining the open pores of the porous construct.

In accordance with yet another embodiment, a surface layer is provided comprising a machined reticulated structure and a powder bonded to a machined tissue-interfacing outer surface of the reticulated structure. The powder comprises asymmetric titanium particles with a size of between about 75 microns and about 106 microns.

In accordance with another embodiment, a surface layer is provided comprising a previously machined reticulated structure to which one or more additional layers of powder have been applied to all surfaces of the previously machined reticulated structure. A powder comprising asymmetric titanium particles with a particle size of between about 75 microns and about 106 microns can be bonded to a machined tissue-interfacing outer surface of the reticulated structure.

In accordance with still another embodiment, a method for increasing the surface roughness of a porous structure is provided. The method comprises machining a porous structure to a desired shape and bonding a powder, comprising asymmetric powder particles, to a machined tissue-interfacing outer surface of the machined porous structure. The powder particles are sized to increase the roughness of the machined tissue-interfacing outer surface of the machined porous structure, while preventing the occlusion of the pores of the porous structure and/or maintaining the porosity of the porous structure. In one embodiment, the porous structure is a porous metal foam and the powder comprises a metallic powder. In another embodiment the porous structure and powder are of a non-metallic material.

In accordance with yet another embodiment, a method for increasing the surface roughness of a porous structure is provided. The method comprises machining a porous structure to a desired shape and applying one or more additional layers of powder to all surfaces of the porous structure. The method also comprises bonding a powder, comprising asymmetric powder particles, to a previously machined tissue-interfacing outer surface of the machined porous structure, said powder particles being sized to increase the roughness of the previously machined tissue-interfacing outer surface of the machined porous structure, while preventing the occlusion of the pores of the porous structure and/or maintaining the porosity of the porous structure.

BRIEF DESCRIPTION OF THE DRAWINGS

The invention will be described herein below by means of example embodiments which are explained in detail with reference to the drawings, in which.

DETAILED DESCRIPTION OF THE PREFERRED EMBODIMENTS

Figure 1:
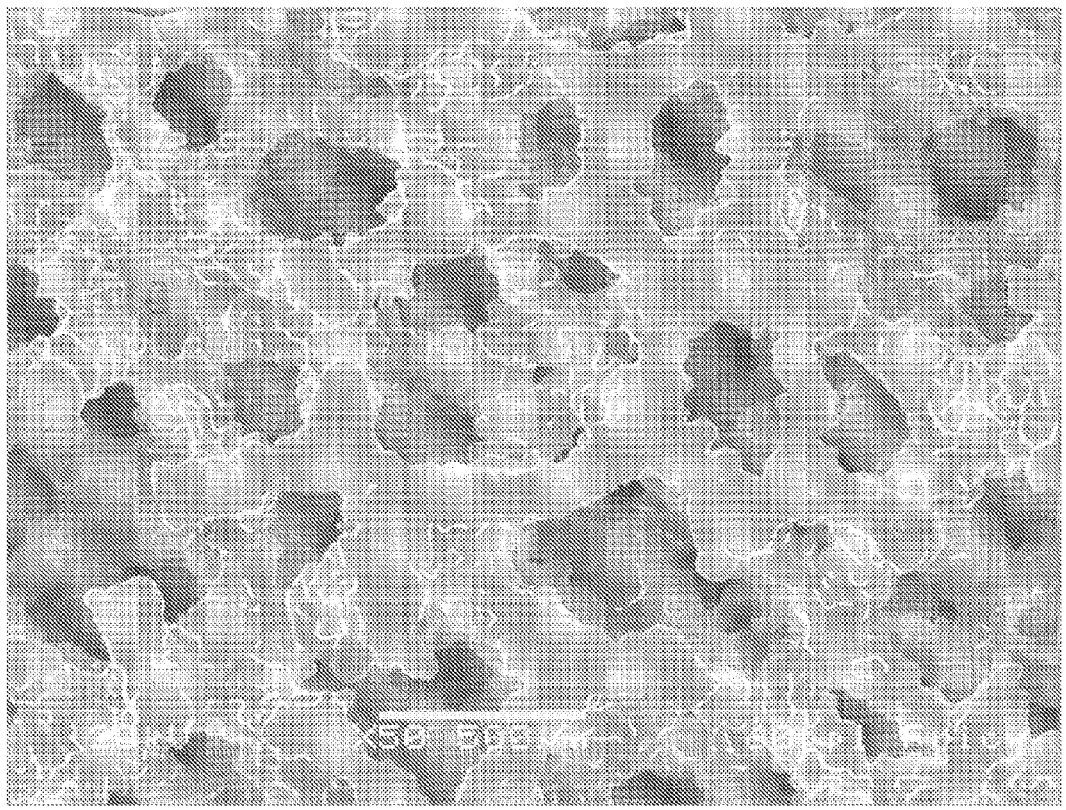
FIG. 1 depicts an enlarged image of a sintered metal foam pre-form of the prior art. The sintered metal foam pre-form shown in FIG. 1 is formed using the steps of: 1) providing a 60 ppi polyurethane (PU) foam skeleton, 2) using a binder, coating said 60 ppi polyurethane (PU) foam skeleton on all of its surfaces with three layers of fine spherical metallic powder (e.g., spherical titanium powder) to create a "Pre-form A", 3) subsequently burning out the PU skeleton from "Pre-form A" as described in reference to Table 1 at 50× magnification to form a green metal foam, 4) subsequently machining said green metal foam to a desired shape using a wire electrical discharge machining (WEDM) process, and then 5) subsequently sintering the machined green metal foam to form said prior art sintered metal foam pre-form.

The embodiments disclosed herein provide a porous structure with increased surface roughness on a machined tissue-interfacing outer surface of the structure and methods of fabricating the same. The machined tissue-interfacing outer surface generally benefits from an increased roughness created by the application of a powder to a porous structure (e.g., porous metal body, porous foam material).

Generally, a tissue-interfacing outer surface with increased roughness can be applied to a porous metallic structure, a formed structure, the surface of a pre-formed structure, or some other object. In the case of medical articles, a bioinert material such as titanium, titanium alloys, tantalum, tantalum alloys, cobalt-chromium alloys, zirconium, zirconium alloys, and the like can be used for the porous structure. However, other suitable metallic and non-metallic materials can be used. Such non-metallic materials can include osteoconductive ceramics such as, for example, calcium phosphates (e.g., alpha and beta tricalcium phosphates, hydroxyapatite, etc). The material may be molded, machined, or processed in any known manner to a desired shape. Further, the material may be solid, in foam form (such as, for example, polyurethane foam), or a foam previously applied to a solid metal substrate composed e.g. of titanium, titanium alloys, tantalum, tantalum alloys, cobalt-chromium alloys, zirconium, zirconium alloys, or other suitable metallic and non-metallic materials.

Notably, as discussed above, machining (e.g. wire electrical discharge machining ("WEDM")) can reduce the surface roughness initially provided to a structure. When the structure is for example a medical article to be implanted in bone, the reduced roughness can decrease any scratch-fit against the bone surface and reduce implant stability. As discussed above, roughness can be recovered using textured molds or using WEDM to cut grooves into the structure. Additionally, as known in the art, surface roughness can be recovered following machining with fine powder (e.g., particle size <45 μm) layer(s) that can be applied to all surfaces of a pre-form foam structure. However, this process does not achieve the desired level of surface roughness in the machined tissue-interfacing outer surface of the pre-form foam structure (see Table 1, below) to increase the scratch-fit of the pre-form structure against an interfacing surface (e.g., bone). Moreover, such a process disadvantageously reduces the porosity of the pre-form structure, which may result in the clogging or occlusion of the pores in the pre-form structure, thereby reducing the ability of bone to intergrow within the porous structure.

In some embodiments the powder can be chosen to optimally increase roughness while maintaining pores open to the surface. In a preferred embodiment a coarse powder having a particle size of between about 75 and 106 μm can be applied to a machined tissue-interfacing outer surface of the pre-form metal foam structure, as further described below, to increase the roughness of said tissue-interfacing outer surface without altering the porosity and pore size of the porous structure. However, said coarse particles can have other suitable sizes. In one embodiment, the porous structure can have a porosity of between about 40% and about 85%. In another embodiment, the porous structure can have a porosity of between about 60% and about 80%.

In one embodiment, the porous structure can have an average pore size of between about 50 μm and about 1000 μm measured using a scanning electron microscope (SEM) or 2D metallographic techniques. In another embodiment, the porous structure can have an average pore size of between about 100 μm and about 500 μm. In still another embodiment, the porous structure can have an average pore size of about 200 μm. However, the porous structure can have other pore sizes. Additionally, the pore size of the porous structure (e.g., polyurethane foam) used to create the pre-form metal foam can be varied to affect the end pore size.

In a preferred embodiment, the size of the coarse powder particles can be between about 10% and 30% of the pore size of the porous structure. In another embodiment, the size of the coarse powder particles can be between about 30% and 70% of the pore size of the porous structure. In still another embodiment, the size of the coarse powder particles can be between about 40% and about 60% of the pore size of the porous structure. However, the coarse powder particles can have other suitable sizes relative to the pore size of the porous structure so as to allow particles that are not bound to the machined tissue-interfacing outer surface of the porous structure to easily pass through the pores of the porous structure to inhibit (e.g., prevent) the clogging or occlusion of the pores in the porous structure.

The powder particles can be applied by dipping, spraying, sprinkling, electrostatic methods, or any other appropriate methods. In one embodiment, a binder can be applied to the machined tissue-interfacing outer surface of the machined metal foam structure. The porous structure can then be dipped into a layer of coarse powder particles to coat the machined tissue-interfacing outer surface with said coarse powder particles. In another embodiment, the coarse powder particles can be sprinkled onto the machined tissue-interfacing outer surface of the porous structure after the binder has been applied to said surface. As discussed above, the coarse powder particles are preferably sized to allow particles that do not adhere to the tissue-interfacing outer surface to easily pass through the porous structure so as to inhibit (e.g., prevent) the clogging or occlusion of the pores in the porous structure. In still another embodiment, the coarse powder particles can be sprayed onto the machined tissue-interfacing outer surface of the porous structure after the binder has been applied to said surface.

Further, the powder can have other properties. In one embodiment the coarse powder particles can be generally asymmetric, which can provide additional roughness for a given particle size. The fine and coarse powders can be of a variety of materials, such as titanium powder, commercially pure titanium powder ("cpTi"), titanium hydride, and titanium dehydride. However the powder can include other suitable metallic materials, such as titanium alloy, cobalt-chrome alloy, tantalum, zirconium, and zirconium alloy, and suitable non-metallic materials, such as calcium phosphates, hydroxyapatite, etc.

The fine and coarse powder can be applied by a variety of methods. For example, a binder can first be applied to the porous structure, such as a polyurethane foam. Then, a layer of powder can be applied to the porous structure. The porous structure can then be sintered such that the powder bonds to the structure. In other embodiments, the metal foam structure to which the fine and coarse powder particles have been applied can be attached to some other structure (e.g., implant substrate), if desired.

More specifically, in one embodiment a polyurethane foam can be provided, which can be cut to a desired size. The cut polyurethane foam can then be impregnated with a binder. A fine powder, such as cpTi, can then be applied to all surfaces of the polyurethane foam to form a starting metal foam structure. In one embodiment, the fine powder can be applied in one or two layers, or more if desired, with binder applied to the porous structure before application of each layer of powder. In another embodiment, the fine powder can be applied in one to four layers, or more if desired. Preferably, the fine powder is applied in sufficient layers to the polyurethane foam to form a porous structure having the desired characteristics (e.g., cell size, interconnecting pore size, average pore diameter, porosity, strength) for a particular application (e.g., medical applications where the structure provides for bone ingrowth) after the final sintering step. As used herein, a pore can be an interstitial pore in the exterior or interior of the foam or porous structure, struts can be the structural elements that define the pores, and the cell can be the volume defined by struts with the pores defined on an outer circumference of the cell. The starting metal foam is then heated at a temperature substantially above the decomposition temperature of polyurethane to burn out the polyurethane and form a green metal foam structure. The green metal foam structure can then be machined (e.g. WEDM) to desired shape to form a pre-form metal foam structure, which as described above, can result in a reduction of the roughness of the machined tissue-interfacing outer surface of the pre-form metal foam structure. In one embodiment, the number of layers of powder applied to the polyurethane foam prior to machining or wire EDM is just enough to increase foam strength to allow for machining of the green metal foam structure while inhibiting damage to the foam structure.

Following the machining of the green metal foam structure, additional layers of fine powder can in one embodiment be applied to all surfaces of the pre-form metal foam structure to further strengthen and roughen the porous structure in order to achieve a desired structure strength and pore size (e.g., for a particular application) upon final sintering. Again, the powder here can be applied in one or more layers, as desired.

Once the machined pre-form metal foam structure has the desired strength and pore size (e.g., via the application of powder layers, as discussed above), a binder can be applied to a machined tissue-interfacing outer surface of the porous structure. In a preferred embodiment, one or more layers of coarse powder particles (e.g., asymmetric particles) can be applied to the binder-coated machined tissue-interfacing outer surface of the pre-form metal foam structure, as described above, to form a roughened pre-form. The coarse powder particles can be applied to the binder-coated machined tissue-interfacing outer surface by spraying, brushing, or sprinkling the coarse powder onto the binder-coated outer surface, or by dipping the binder-coated outer surface into a layer of coarse powder. The coarse powder can then be sintered onto the binder-coated outer surface to form a roughened metal foam. In another embodiment, the metal powder particles can be coated with binder and applied to the machined tissue-interfacing outer surface of the pre-form metal foam structure. In one embodiment, the roughened pre-form structure can be attached to a substrate before the coarse powder is sintered onto the binder-coated outer surface of the roughened pre-form structure.

In another embodiment, a porous titanium foam pre-form that has been machined to size can be provided. A layer of binder can be applied to the machined tissue-interfacing outer surface of the pre-form structure, followed by a coarse metal powder (such as, for example, cpTi or titanium hydride), to form a roughened pre-form structure. The roughened pre-form structure can then be put through a final sintering, bonding the coarse powder to the pre-form to produce a roughened metal foam structure.

Samples of machined and sintered titanium foam pieces with and without added powder layers have been tested. The texture of the machined tissue-interfacing outer surface of the samples was determined by measuring the coefficient of linear friction of said surface. The linear friction was measured against rigid polyurethane foam (used to simulate cancellous bone) using an orthopedic friction and wear testing machine (OrthoPod), where a normal load of approximately 44 N was applied to the sample part against the polyurethane foam and the foam rotated in an arc shaped motion at a displacement rate of about 3.8 mm/sec. Further details of the linear friction test methodology used can be found in "Friction Evaluation of Orthopedic Implant Surfaces Using a Commercially Available Testing Machine," Gilmour et al., abstract #464 World Biomaterials Congress 2008, the contents of which are incorporated herein by reference in their entirety and should be considered a part of this specification, and which is attached as Appendix A.

Table 1 shows the friction results for three types of sintered Ti foam surfaces: (1) a pre-form machined by WEDM from a green metal foam formed by coating a 60 ppi PU foam on all its surfaces with three layers of fine (<45 μm) spherical Ti powder, in which all three layers were applied before machining ("Pre-form A"), illustrated in FIG. 1; (2) a pre-form machined by WEDM from a green metal foam formed by coating a 60 ppi PU foam on all its surfaces with three layers of fine (<45 μm) spherical Ti powder, in which two powder layers were applied before machining and one was applied after machining ("Pre-form B"), illustrated in FIG. 2; and (3) Pre-form A with one layer of coarse (75-106 μm) asymmetric Ti (Ti dehydride) powder applied after machining to the outer tissue-interfacing surfaces ("Roughened Metal Foam"), illustrated in FIGS. 3-4. As shown, the surface with a large asymmetric powder applied after machining had the highest coefficient of linear friction as compared to the other surfaces.

TABLE 1

| Linear Friction Testing (n = 3 per group) | |
|---|---|
| Test Sample | Coefficient of Linear Friction |
| Pre-form A | 0.90 ± 0.09 |
| Pre-form B | 0.98 ± 0.02 |
| Roughened Metal Foam | 1.09 ± 0.10 |

FIG. 1 shows sintered metal foam "Pre-form A" where the machined tissue-interfacing outer surface of the porous metal foam structure has not been roughened, as discussed in embodiments herein. The pre-form metal foam structure has a cell size diameter of approximately 600 μm with interconnecting pores of approximately 200 μm in diameter. The overall average pore diameter (mean void intercept length (MVIL)) is approximately 464.4±95.4 μm. The average thickness of a strut (e.g., the support element that defines the cell) of the non-roughened metal foam is approximately 150 μm. The average gravimetric porosity of the metal foam was 75.2±2.7%. Linear friction tests of the machined tissue-interfacing outer surface of "Pre-form A" resulted in a maximum linear friction coefficient of 0.90±0.09.

Figure 2:
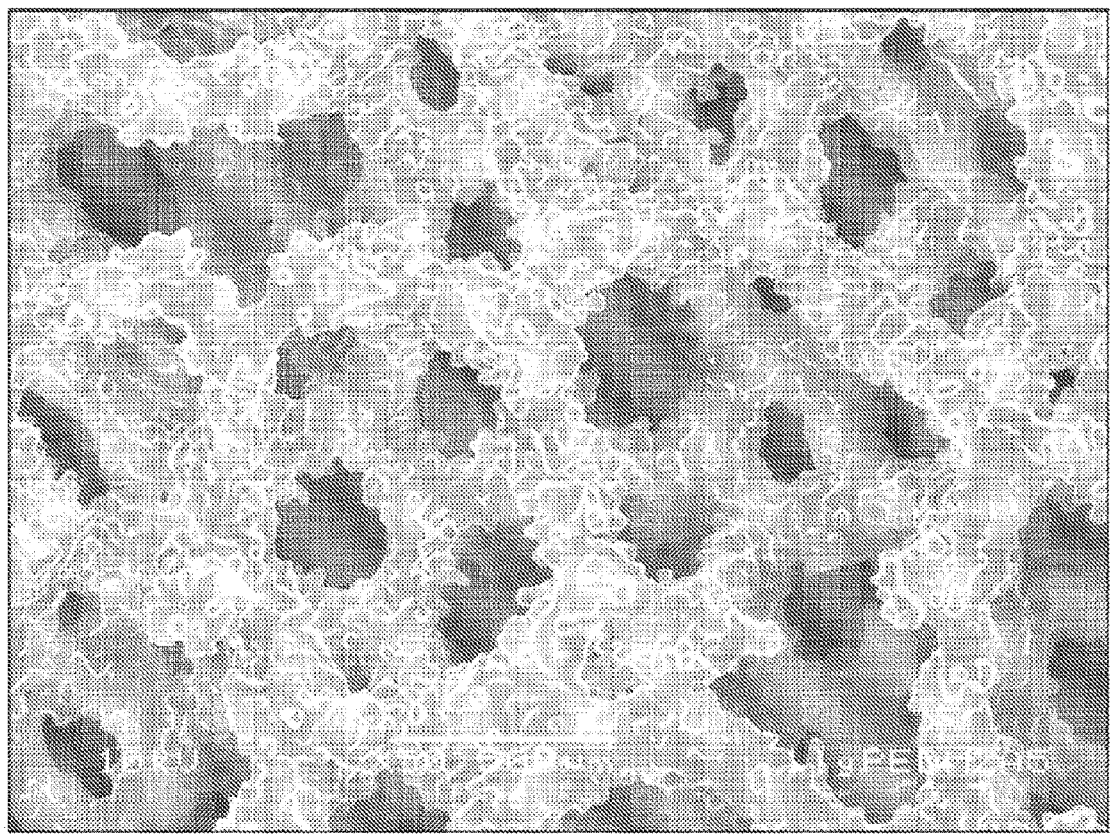
FIG. 2 depicts an enlarged image of an improved sintered metal foam pre-form according to one embodiment of the present invention. The improved sintered metal foam pre-form shown in FIG. 2 may be formed using the steps of: 1) providing a 60 ppi polyurethane (PU) foam skeleton, 2) using a binder, coating said 60 ppi PU foam skeleton on all of its surfaces with two layers of fine spherical metallic powder (e.g., spherical Ti powder), 3) subsequently burning out the PU skeleton from the resulting construct to form a green metal foam, 4) subsequently machining said green metal foam to a desired shape using a wire electrical discharge (WEDM) process or the like to form a machined green metal foam, 5) subsequently applying an additional layer of fine spherical metallic powder (e.g., spherical Ti powder) to all surfaces of said machined green metal foam to form a "Pre-form B" as described in reference to Table 1 at 50× magnification, and then 6) subsequently sintering the Pre-form B to form said improved sintered metal foam.

FIG. 2 shows sintered metal foam "Pre-form B" with a fine metal powder applied to all surfaces of the machined porous metal foam structure (i.e., the pre-form metal foam structure). Pre-form B in FIG. 2 includes one layer of fine (<45 μm) spherical cpTi powder applied to the all surfaces of the pre-form structure after machining of the green metal foam structure. Linear friction tests of the machined tissue-interfacing outer surface of "Pre-form B" with the layer of fine spherical Ti powder applied after machining resulted in a maximum linear friction coefficient of 0.98±0.02.

Figure 3:
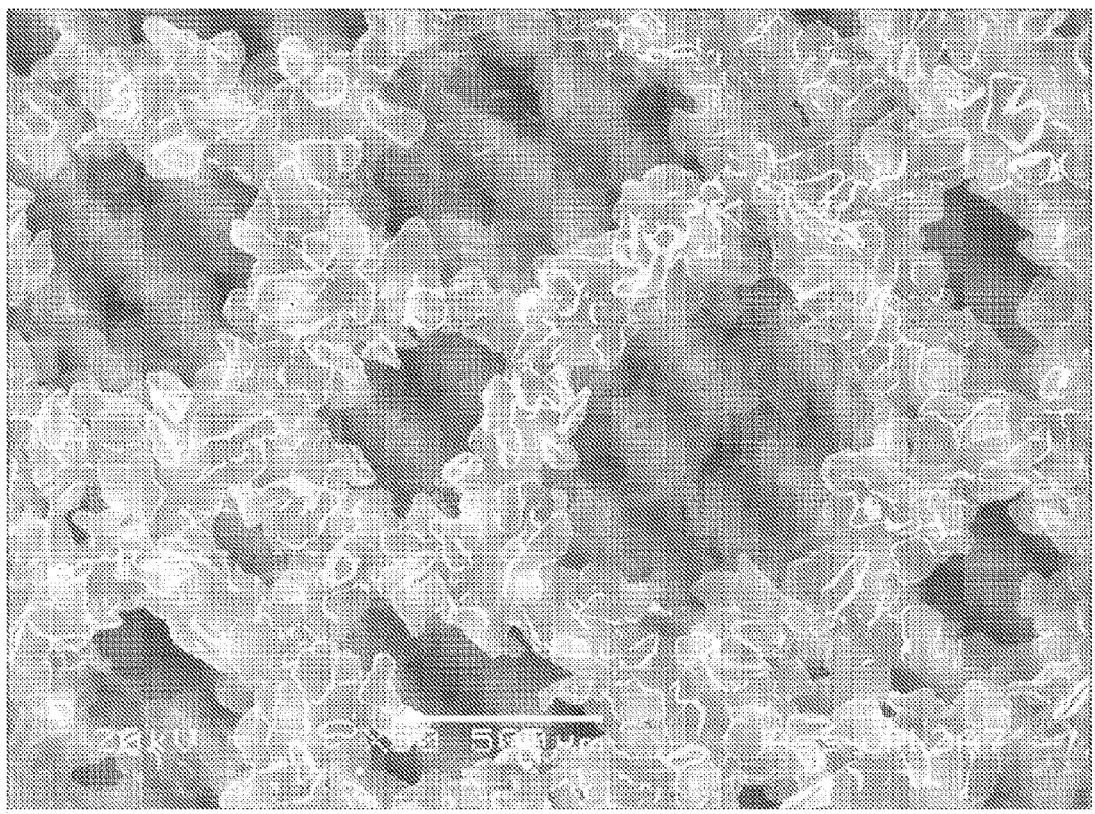
FIG. 3 depicts an enlarged image of a "roughened metal foam" according to another embodiment of the present invention. The "roughened metal foam" may be formed using the steps of: 1) providing "Pre-form A" as discussed above, 2) machining "Pre-form A" to a desired shape using a wire electrical discharge machining (WEDM) process or the like, wherein the step of machining forms at least one machined tissue-interfacing outer surface, 3) applying at least one layer of asymmetric metallic powder particles (e.g., titanium or Ti dehydride particles) to said at least one machined tissue-interfacing outer surface as described in reference to Table 1 at 50× magnification, and 4) sintering the resulting construct to form said "roughened metal foam"
Figure 4:
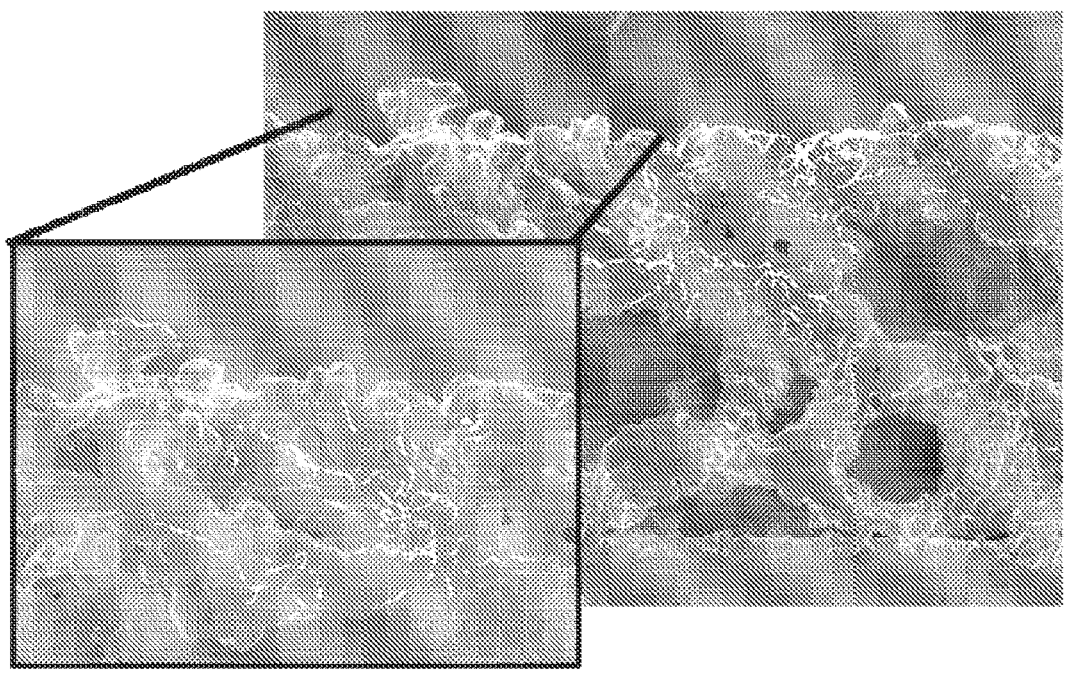
FIG. 4 is an enlarged image of a cross-section of the Roughened Metal Foam of FIG. 3 showing a roughened porous metal foam structure with a roughened tissue-interfacing outer surface at 50× magnification (large image) and 85× magnification (inset image)

FIGS. 3 and 4 illustrate a sintered "Roughened Metal Foam" structure with a roughened machined tissue-interfacing outer surface achieved according to a preferred embodiment of the invention. As shown in FIGS. 3-4, a layer of metal powder was applied to the machined tissue-interfacing outer surface of a pre-form metal foam structure such that the overall pore size and porosity of the porous metal foam are not substantially altered. The metal powder applied to the pre-form metal foam illustrated in FIGS. 3 and 4 for increasing the roughness of the machined tissue-interfacing outer surface of the pre-form metal foam was asymmetric titanium powder with particles approximately 75-106 μm in size. Because the powder was applied only to the machined tissue-interfacing outer surface, the average cell size diameter and interconnecting pore size was not substantially different from the pre-form metal foam structure following application of the powder (e.g., MVIL of Roughened Metal Foam is approximately 448.9±34.5). Furthermore, the average gravimetric porosity of the roughened pre-form metal foam structure was substantially unchanged from that of the pre-form metal foam structure and is approximately 75.3±2.2%. Linear friction tests of the machined tissue-interfacing outer surface of the "Roughened Metal Foam" with the layer of coarse asymmetric Ti powder applied after machining resulted in a maximum linear friction coefficient of 1.09±0.10.

Figure 5:
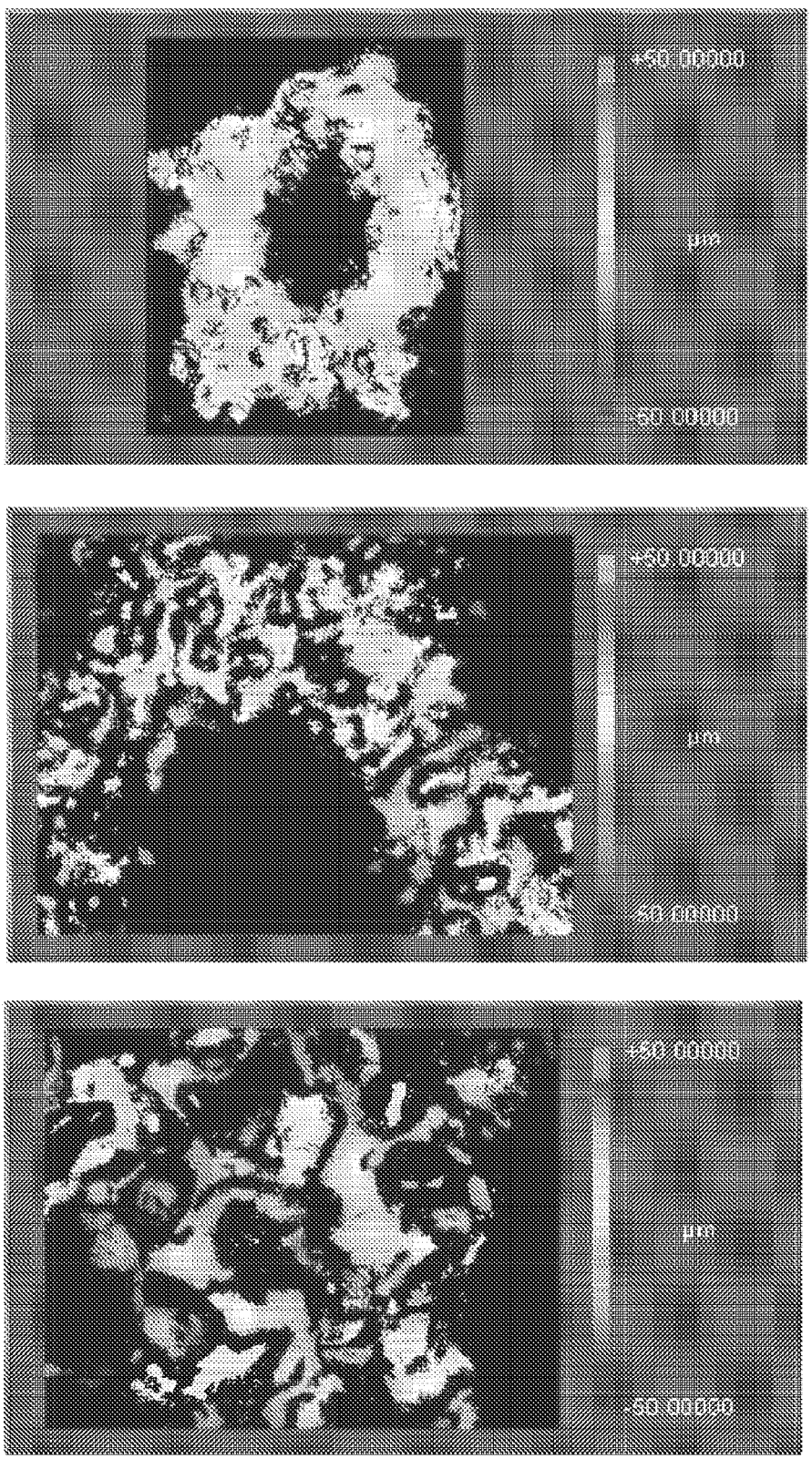
FIG. 5 depicts topographical relief maps of the outer tissue-interfacing surfaces of "Pre-form A", "Pre-form B, and "Roughened Metal Foam", respectively, as described in reference to Table 2.

As depicted in FIG. 5, white light interferometry was used to determine the difference in surface roughness of the metal foam struts on the machined tissue-interfacing outer surface of the sintered Ti Foam structures under the following conditions: "Pre-form A" (Wire EDM Surface) shown in FIG. 1; "Pre-form B" (Wire EDM surface plus one layer of fine spherical Ti powder on all surfaces after machining of the green state metal foam structure), as shown in FIG. 2; and "Roughened Metal Foam" (Pre-form A plus one layer of coarse (75-106 μm) asymmetric Ti (Ti dehydride) powder applied to the outer tissue-interfacing surfaces after machining of the green state metal foam structure), as shown in FIGS. 3-4. The results are given in Table 2, with "Ra" representing the average roughness of all points from a plane fit to the test part surface, and "SRz" representing the average of the largest half of the radial peak-to-valley areal roughness results. The Roughened Metal Foam Ti Foam surface had the largest roughness values, followed by the Ti Foam "Pre-form B" with the fine spherical powder applied to all surfaces after machining of the green state metal foam structure and the machined "Pre-form A" Ti Foam. These results are reflective of the tactile feel of the surfaces, with the large asymmetric powder coated Ti Foam sample having the roughest feel.

TABLE 2

White Light Interferometry Results

| Test Sample | Ra (μm) | SRz (μm) |
| --- | --- | --- |
| Pre-form A | 2.3 ± 0.5 | 19.6 |
| Pre-form B | 6.2 ± 0.7 | 40.6 |
| Roughened Metal Foam | 9.9 ± 2.1 | 57.7 |

With reference to FIG. 1, white light interferometry roughness measurements of the machined tissue-interfacing outer surfaces of the "Pre-form A" metal foam structure resulted in an average roughness (Ra) of 2.3±0.50 μm.

With reference to FIG. 2, white light interferometry roughness measurements of the machined tissue-interfacing outer surface of the "Pre-form B" metal foam structure with said additional layer of fine spherically-shaped metal particles applied to all surfaces of the pre-form structure resulted in an average roughness (Ra) of about 6.2 μm.

With reference to FIGS. 3-4, white light interferometry roughness measurements of the roughened metal foam structure resulted in an increase in average roughness (Ra) of 9.9±2.1 μm, significantly greater than the roughness of either non-roughened metal foam (Pre-form A or Pre-form B).

A summary of the properties describing the pre-form metal foam structure and roughened metal foam structure as shown in FIGS. 1 and 3-4, respectively, is given in Table 3.

TABLE 3

Properties of Sintered Pre-form Metal Foam and Roughened Metal Foam

| | Pre-form A Metal Foam | Roughened Metal Foam |
| --- | --- | --- |
| Cell Size Diameter (microns) | ~600 | ~600 |
| Interconnecting Pore Size (microns) | ~200 | ~200 |
| Average Pore Diameter (MVIL) (microns) | 464.4 ± 95.4 | 448.9 ± 34.5 |
| Gravimetric Porosity (%) | 75.2 ± 2.7 | 75.3 ± 2.2 |
| Strut Roughness (Ra) (microns) | 2.3 ± 0.50 | 9.9 ± 2.1 |
| Maximum Coefficient of Friction | 0.90 ± 0.09 | 1.09 ± 0.10 |

Of the powders used to roughen the Ti Foam surface, the Titanium Dehydride Powder—140+200 Mesh (75-106 μm), resulted in the bone interface surface with the highest friction, largest roughness value, and roughest texture as assessed by tactile feel.

In other embodiments, the pre-form metal foam structure can have variations in pore size and strut thickness. Additionally, the powder applied to the machined tissue-interfacing outer surface to increase its roughness can, in other embodiments, have a particle size greater than 106 μm or smaller than 75 μm. In another embodiment, the shape of the metal powder particles deposited on the machined tissue-interfacing outer surface of the pre-form metal foam structure can be shapes other than asymmetric. Additionally, the metal powder particles need not have a uniform shape.

Additional variations can involve the types of powder used and steps taken after the application of the powder. For example, different types and sizes of powder can be applied to different portions of an implant, for example where different portions of the implant will interface with different types of tissue. Further, different types and sizes of powder can be layered, so as to produce, for example, a fractal-like effect of roughness at varying sizes overlaid on one-another. Varying roughness sizes can allow different mechanisms of attachment with surrounding body tissue, such as simultaneously allowing tissue ingrowth at a macroscopic scale, while also allowing cellular adhesion to an implant surface at a smaller scale. To accomplish such varying roughness sizes, the different powders can be applied sequentially, creating for example a size gradient with a top surface of small-scale roughness and larger roughness directly beneath. Alternatively, in one embodiment the different powders can be applied simultaneously, creating a heterogeneous mix of roughness sizes.

Figure 6:
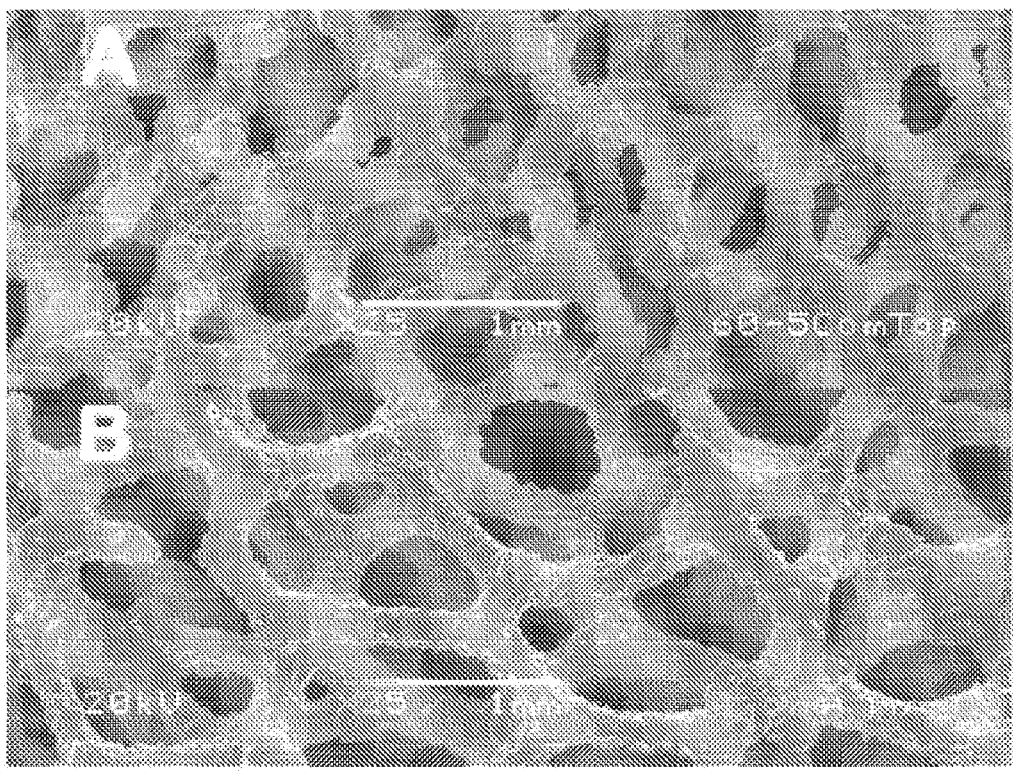
FIG. 6 shows SEM images (25×) of machined and sintered metal foam produced using (A) 60 ppi starting polyurethane foam and (B) 45 ppi starting polyurethane foam, with reference to Table 4.

In some embodiments, as the pore size increases, the strut thickness can also increase (see Table 4 and FIG. 6). Both properties dictate the size range of powder that can be used to roughen the machined tissue-interfacing outer surface of the pre-form metal foam structure while maintaining an open surface porosity. The powder applied to the tissue-interfacing outer surface of the pre-form metal foam structure is preferably sized to inhibit (e.g., prevent) surface pore occlusion. In a preferred embodiment, powder applied to the tissue-interfacing outer surface of the machined foam metal structure has a size of approximately <100% of the strut thickness and about <50% of the pore size, so as to advantageously inhibit pore occlusion.

TABLE 4

Pore Size and Strut Thickness for Two Metal Foams of Different Pore Densities. (Note: Starting Polyurethane Foam was coated with the same number of metal powder layers to produce the 60 pores per inch (ppi) and 45 ppi Pre-form Metallic Foams.)

| Starting Polyurethane Foam Density | Pore Size (MVIL) (microns) | Strut Thickness (microns) |
|---|---|---|
| 60 ppi | 464.4 ± 95.4 | 146 ± 26 |
| 45 ppi | 618.4 ± 57.9 | 365 ± 73 |

The shape and size of the surface roughening powder affects the roughness and frictional values of the roughened metal foam. Roughness and friction properties of a sintered Pre-form A metal foam structure (a WEDM surface) and a sintered Pre-form B metal foam structure (a WEDM surface with a layer of fine (<45) spherical powder applied after machining to all surfaces) are compared to Roughened Metal Foam with either fine asymmetric powder (<45 atm) or coarse asymmetric powder (75-106 µm), as shown in Table 5.

TABLE 5

Properties of Sintered Pre-form Metal Foams A and B (Not Roughened), Fine Asymmetric Powder Roughened Metal Foam, and Coarse Asymmetric Roughened Metal Foam

|  | Pre-form A Metal Foam | Pre-form B Metal Foam | Fine Asymmetric Roughened Metal Foam | Coarse Asymmetric Roughened Metal Foam |
|---|---|---|---|---|
| Strut Roughness (Ra) (microns) | 2.3 ± 0.50 | 6.2 ± 0.70 | 6.4 ± 0.98 | 9.9 ± 2.1 |
| Maximum Coefficient of Friction | 0.90 ± 0.09 | 0.98 ± 0.02 | 0.97 ± 0.01 | 1.09 ± 0.10 |

Use of powders also provides advantages over other methods. For example, the application of such powders can be simpler, easier, and cost effective and does not introduce grooves that would result in gaps between the bone and ingrowth structure upon implantation. Unlike overlying grids, the powder can be easily applied to almost any arbitrary geometry. Further, the powders can allow increases of roughness with relative precision (e.g., close tolerances) in regard to the end roughness of the piece, as well as the final geometry of the piece.

The layers described herein can be used with a number of medical articles. For example, the layer can be applied to a bulk metal foam augment to fill a bone void, a metallic foam-coated implant for a knee implant, hip implant, shoulder or spinal application, a tibial tray, acetabular shell, femoral stem, stem collar, other knee femoral components, or other medical implants or articles.

Figure 7:
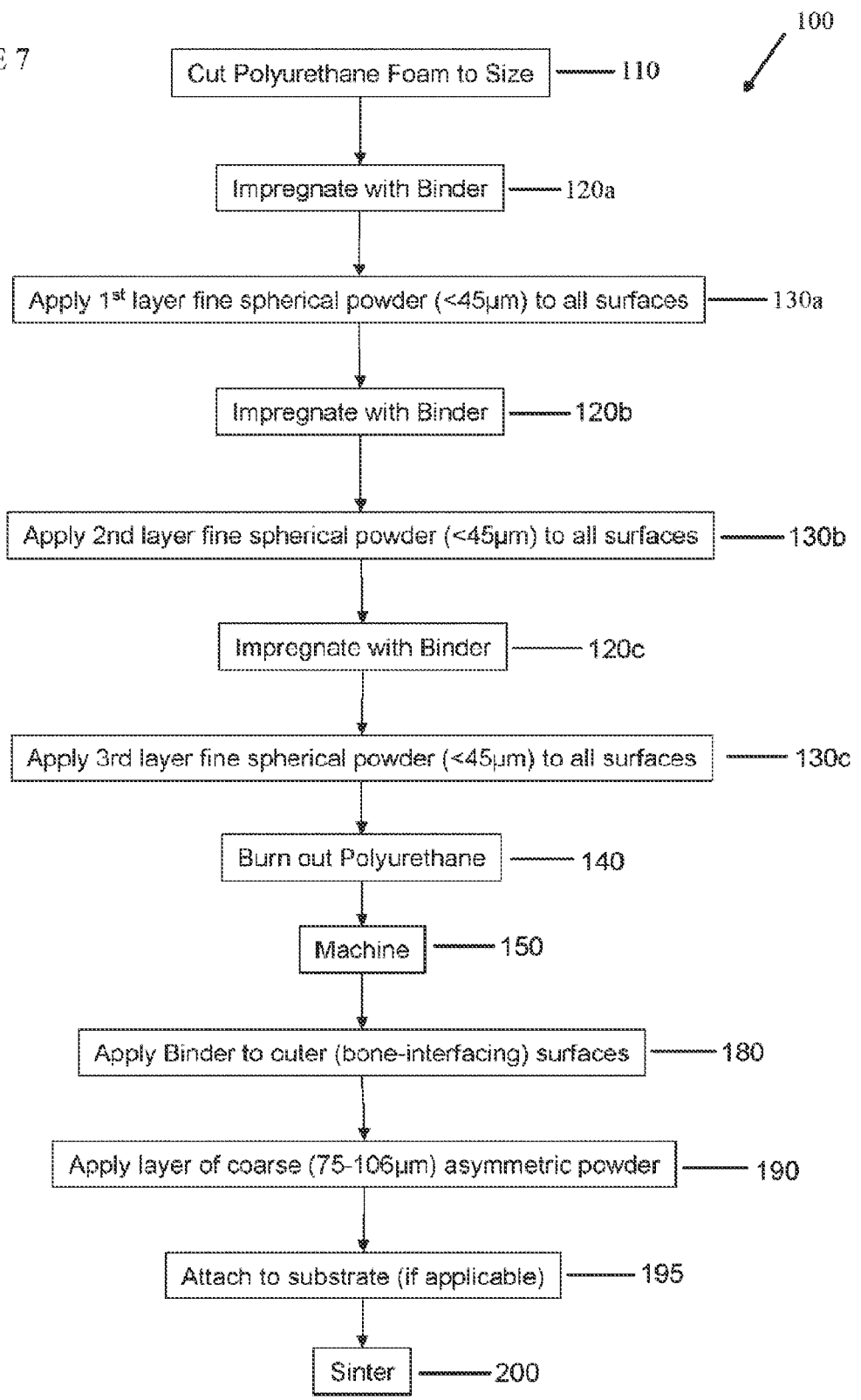
FIG. 7 depicts one embodiment of a method for preparing a porous foam structure with a tissue-engaging outer surface having increased roughness.

FIG. 7 illustrates one embodiment of a method 100 for preparing a roughened metal foam structure with a tissue-engaging machined outer surface having increased roughness without affecting the porosity and pore size of the porous structure. The method 100 includes cutting 110 a polyurethane foam having a desired pore size to a desired size and impregnating 120*a* the foam with a binder (e.g., a thermally decomposing binder), after which a first layer of fine powder (e.g., a bioinert metallic powder such as titanium, titanium alloy, tantalum, tantalum alloy, cobalt-chromium alloys, zirconium, zirconium alloys, etc.) is applied to the foam to form a starting metal foam. In the illustrated embodiment, the fine powder having a particle size of less than 45 µm is applied 130*a* to all surfaces of the porous polyurethane foam. The method 100 further includes impregnating 120*b* the starting metal foam with binder and applying 130*b* a second layer of fine powder, after which the starting metal foam is further impregnated 120*c* with binder and a third layer of fine powder is applied 130*c*. However, more or fewer than three layers of fine powder can be applied so as to achieve the desired characteristics (e.g., pore size and strength requirements) of the starting metal foam, as discussed above. The method 100 additionally includes burning out 140 the polyurethane to provide a green metal foam structure. The green metal foam structure can then be machined 150 to provide a pre-form metal foam structure. The steps 110-150 above for providing a pre-form metal foam structure are known in the art.

Advantageously, in the embodiments of the invention disclosed herein, the method 100 further includes applying 180 a binder to bone-interfacing machined outer surface of the pre-form metal foam structure and applying 190 a layer of coarse asymmetric powder with a particle size of between about 75 µm and 106 µm thereonto to form a roughened pre-form structure. Preferably, the layer of coarse asymmetric powder is deposited only on the bone-interfacing machined outer surface (e.g., the coarse particles are sized relative to the pores so that particles that are not deposited on the bone-interfacing machined outer surface pass through the pores of the metallic foam structure without clogging or occluding the pores of the structure). Though the method 100 discloses applying one layer of coarse powder particles, one of ordinary skill in the art will recognize that any suitable number of layers of coarse metal powder particles can be applied. The method 100 optionally includes attaching 195 the roughened pre-form structure to a substrate. The layer of coarse powder is then sintered 200 on the bone-interfacing outer surfaces of the roughened pre-form structure to form the roughened metal foam.

Figure 8:
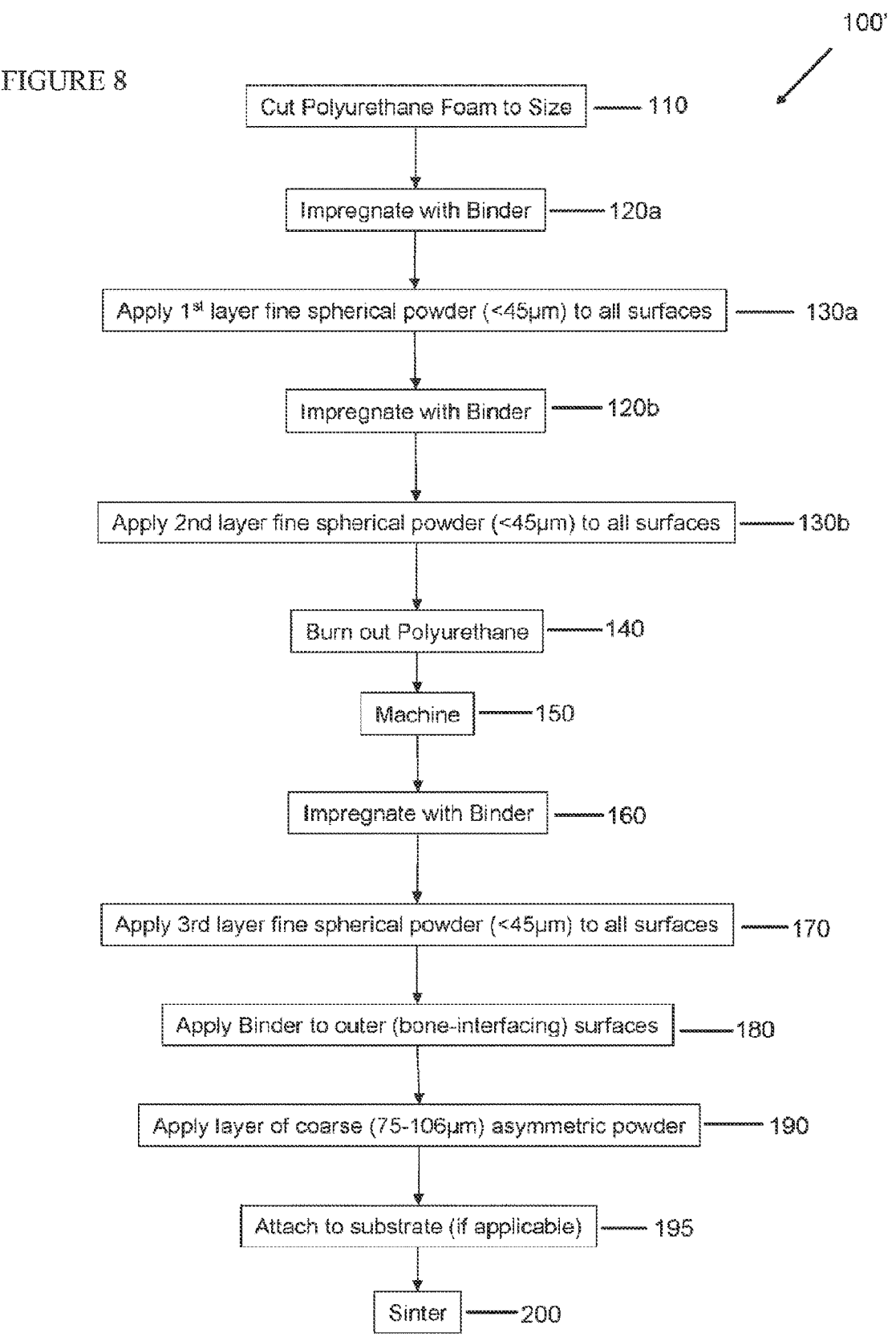
FIG. 8 depicts another embodiment of a method for preparing a porous foam structure with a tissue-engaging outer surface having increased roughness without affecting the porosity and pore size of the porous structure.

FIG. 8 illustrates another embodiment of a method 100' for preparing a porous foam structure with a tissue-engaging outer surface having increased roughness without affecting the porosity and pore size of the porous structure. The method 100' is similar to the method 100 illustrated in FIG. 7 so that similar steps are identified with identical numerical identifiers. The method 100' differs from the method 100 in that the starting metal foam is twice impregnated 120*a*, 120*b* with a binder, and only two layers of fine powder are applied 130*a*, 130*b* to all surfaces of the starting metal before machining of the green state metal foam to provide a pre-form metal foam structure. As discussed above, the process of forming the pre-form metal foam structure is known in the art.

Advantageously, the method 100' includes impregnating 160 the pre-form metal foam structure with binder and applying 170 a third layer of fine powder to all surfaces of the pre-form metal foam structure. However, one of ordinary skill in the art will recognize that any suitable number of layers of metal powder can be applied before and/or after the machining of the green state metal foam structure to achieve the desired characteristics of the metal foam structure, as discussed above. A layer of binder 180 and asymmetric powder 190 is similarly applied and sintered 200 to the machined tissue-interfacing outer surface to increase the roughness of the pre-form metal foam so as to provide a roughened metal foam without altering the overall pore size and porosity of the structure so as to inhibit (e.g., prevent) clogging of the pores in the roughened metal foam structure.

Embodiments of medical implants that can incorporate the roughened tissue-interfacing outer surface on a porous structure, as described in the embodiments above, are depicted in FIGS. 9-12.

Figure 9:
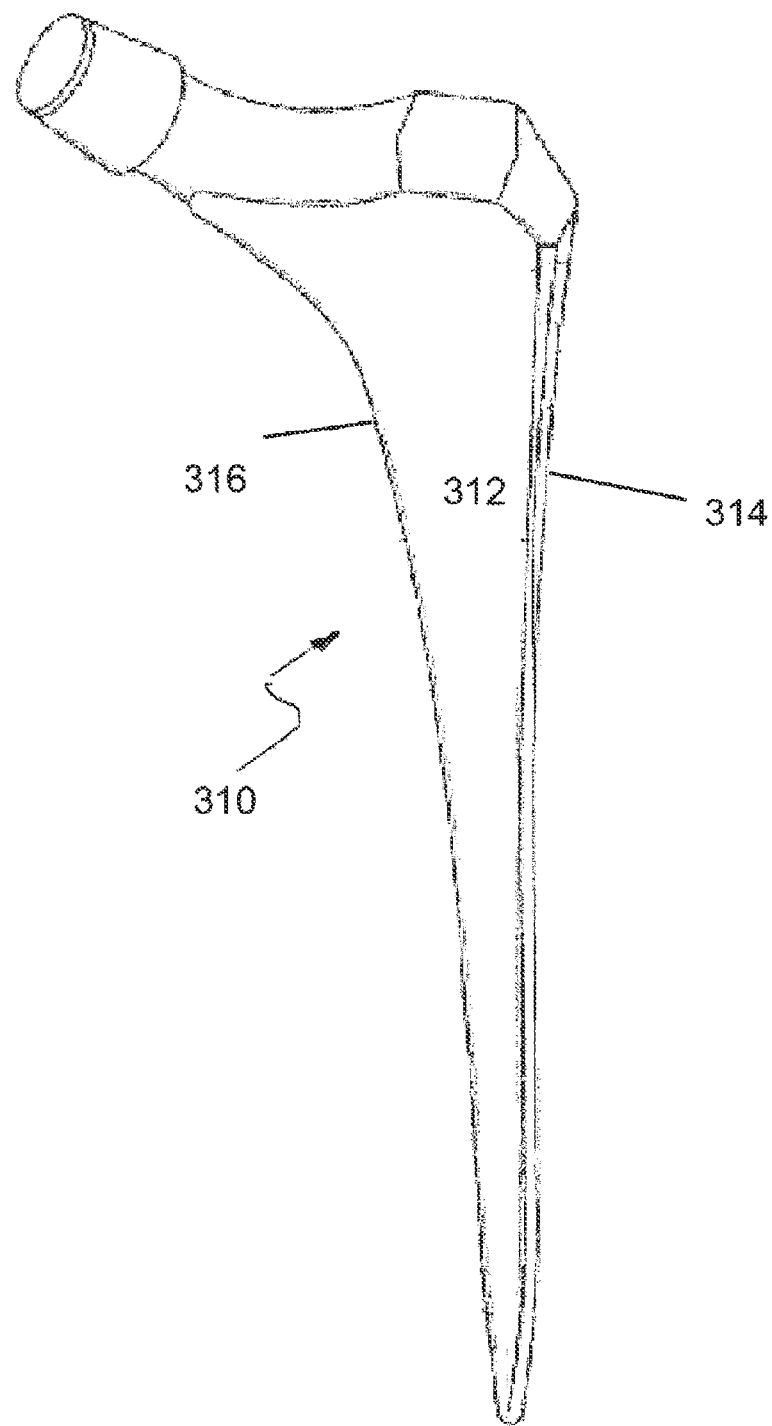
FIG. 9 depicts an embodiment of a femoral stem of a hip joint prosthesis with a roughened tissue-interfacing outer surface.

FIG. 9 depicts an embodiment of a femoral stem 310 of a hip joint prosthesis with a roughened tissue-interfacing porous outer surface, as further described in U.S. Pat. No. 6,540,788, the contents of which are hereby incorporated by reference and should be considered a part of this specification. For example, the outer surface of one or more of the anterior/posterior sides 312, lateral side 314 and medial side 316 of the femoral stem 310 can include a roughened porous structure having a roughened tissue-interfacing outer surface, as described above, to improve its fixation in a femoral cavity. In one embodiment, the substrate material of the femoral stem 310 can undergo a surface treatment (e.g., grit blasting), after which the roughened porous structure (e.g., roughened metal foam, as described above) can be applied to the substrate.

Figure 10:
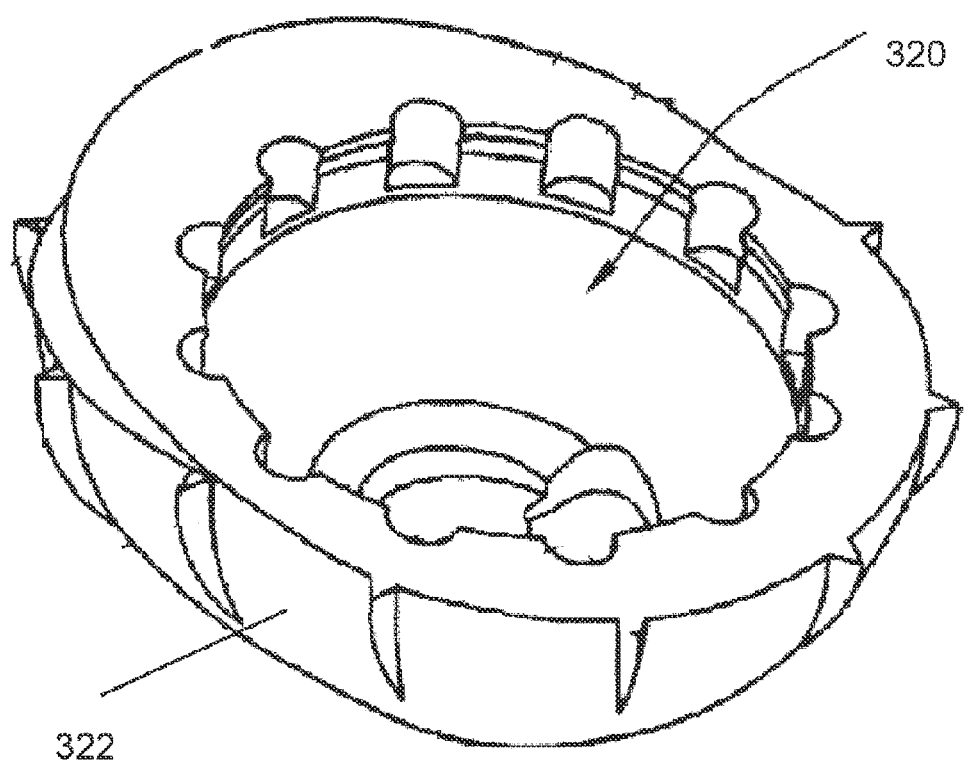
FIG. 10 depicts an embodiment of an acetabular shell of a hip joint prosthesis with a roughened tissue-interfacing outer surface.

Similarly, FIG. 10 depicts an embodiment of an acetabular shell 320 for a hip joint prosthesis, as further described in U.S. Pat. No. 6,537,321, the contents of which are hereby incorporated by reference and should be considered a part of this specification. The outer surface 322 of the acetabular shell 320 can include a roughened porous structure with a roughened tissue-interfacing outer surface, as discussed above, to advantageously increase the scratch fit of the acetabular shell 320 against the bone (e.g., the acetabulum) into which its implanted, as well as allow for bone ingrowth into the porous structure to provide for greater stability of the implanted acetabular shell 320.

Figure 11:
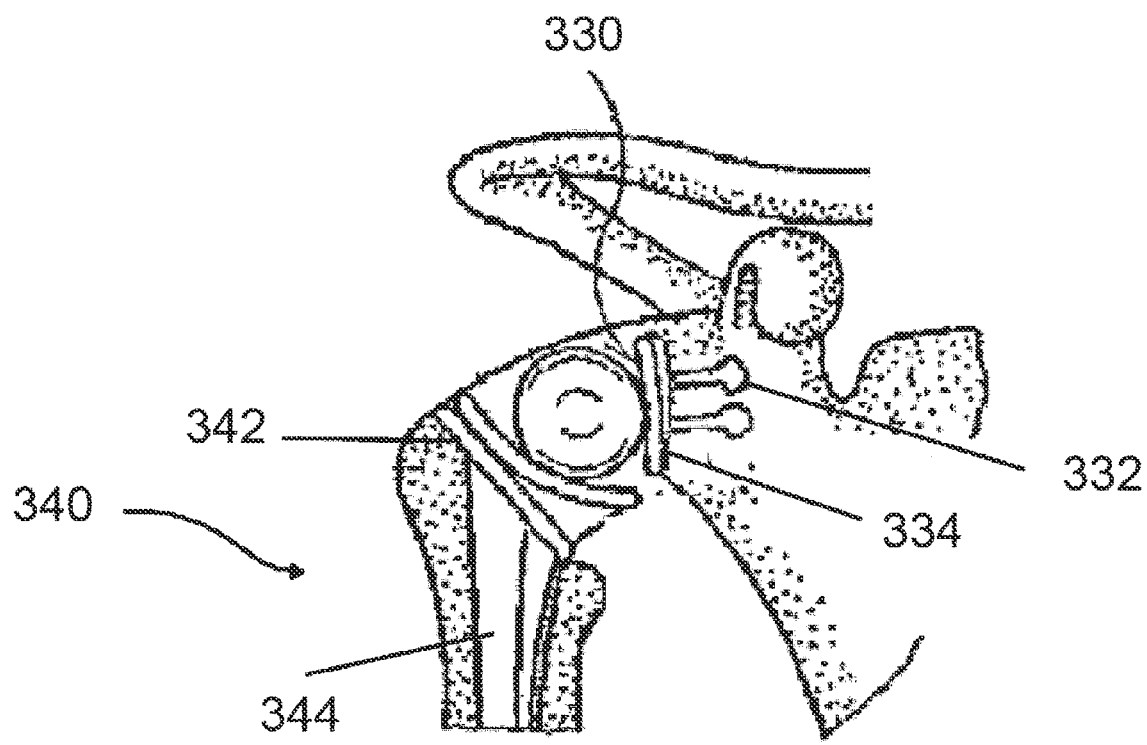
FIG. 11 depicts an embodiment of a shoulder prosthesis with a roughened tissue-interfacing outer surface.

FIG. 11 depicts an embodiment of a shoulder prosthesis including a glenoid prosthesis 330, as further described in U.S. Publication No. 2006-0111787, the contents of which are hereby incorporated by reference and should be considered a part of this specification. The anchoring surfaces 332, 334 of the glenoid prosthesis 330 can include a roughened porous structure with a roughened tissue-interfacing outer surface, to facilitate anchoring of the glenoid prosthesis in the scapula of a shoulder blade. Similarly, bone engaging surfaces 342, 344 of the humerus stem 340 of the shoulder prosthesis can have a roughened porous structure with a roughened tissue-interfacing outer surface, as described in the embodiments above, which can advantageously improve the scratch-fit of the stem in bone, as well as allow bone ingrowth into the porous structure to provide improve stability of the stem following implantation.

Figure 12:
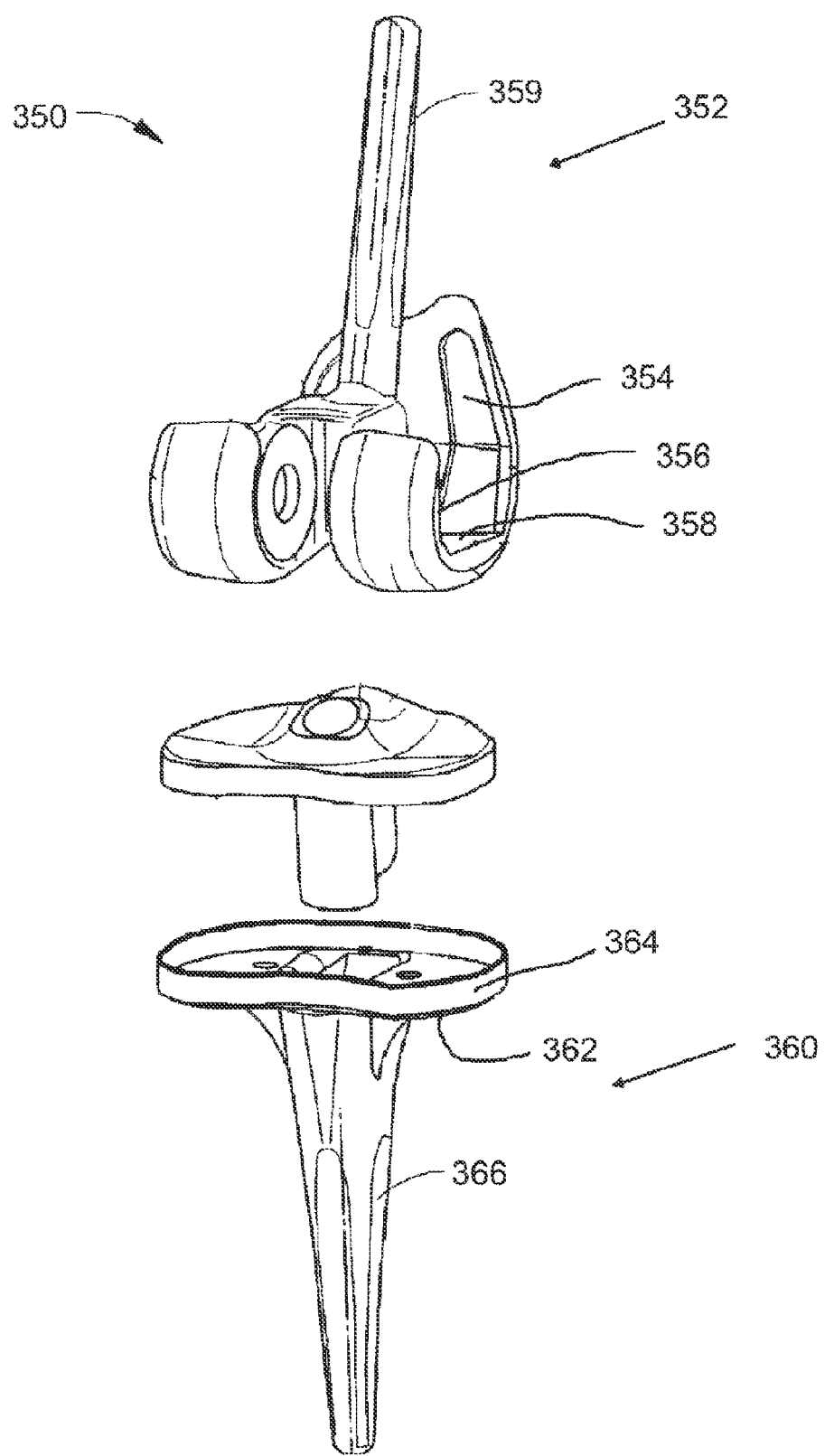
FIG. 12 depicts one embodiment of a knee joint prosthesis with a tissue-interfacing outer.

FIG. 12 depicts an embodiment of a knee joint prosthesis 350 including a femoral component 352 and a tibial component 360, as further described in U.S. Pat. No. 5,954,770, the contents of which are hereby incorporated by reference and should be considered a part of this specification. The bone engaging surfaces of the femoral component prosthesis 352, including the internal anterior 354 and posterior 356 condyle surfaces, the interior surface of the patellar shield 358, and the femoral anchoring stem 359 can include a roughened porous structure with a roughened bone-interfacing outer surface that can be formed as disclosed in embodiments herein. Similarly, bone engaging surfaces of the tibial stem prosthesis 360, including exterior surfaces of the tibia plateau 362, 364 and tibia shaft 366 can include a roughened porous structure with a bone-interfacing outer surface formed as described in the embodiments above, to provide an increase scratch fit of the tibial stem prosthesis 360 in bone, as well as to allow for bone ingrowth into the porous structure, thereby providing improved stability of the tibial stem prosthesis 360 following implantation.

The embodiments of the invention described herein can also be incorporated into a porous augment that can be implanted into a void in bone or can be used to fill a void, crack, cavity or other opening in bone, whether naturally occurring or surgically created.

Although the foregoing systems and methods have been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. While certain embodiments of the inventions have been described, these embodiments have been presented by way of example only, and are not intended to limit the scope of the inventions. Indeed, the novel methods and systems described herein may be embodied in a variety of other forms without departing from the spirit thereof. Accordingly, other combinations, omissions, substitutions and modifications will be apparent to the skilled artisan in view of the disclosure herein.

What is claimed is:

1. A method for increasing the surface roughness of a porous structure, comprising:
   machining a porous structure to a desired shape, the porous structure having a machined tissue-interfacing outer surface having a pore size;
   bonding a powder to the machined tissue-interfacing outer surface of the machined porous structure, the powder comprising asymmetric powder particles; and
   substantially retaining, upon bonding of the powder, the pore size of the machined tissue-interfacing outer surface,
   wherein the asymmetric powder particles are sized to increase the roughness of the machined tissue-interfacing outer surface of the machined porous structure while preventing the occlusion of the pores of the porous structure.

2. The method of claim 1, wherein the asymmetric powder particles are sized from about 75 micrometers to about 106 micrometers.

3. The method of claim 1, further comprising the step of sintering the porous structure.

4. The method of claim 1, wherein the porous structure comprises a bulk metal foam augment.

5. The method of claim 1, further comprising the step of attaching the porous structure to a substrate.

6. The method of claim 5, wherein the substrate is a metallic foam-coated implant selected from the group consisting of a knee implant, hip implant, a shoulder implant, a spinal implant, a tibial tray, an acetabular shell, a femoral stem, and a stem collar.

7. The method of claim 1, further comprising the step of applying one or more additional layers of powder to all surfaces of the porous structure.

8. The method of claim 7, wherein the step of applying one or more additional layers occurs after the step of bonding a powder to a machined tissue-interfacing outer surface of the machined porous structure.

9. The method of claim 7, wherein the one or more additional layers each comprise a fine spherical powder, the fine spherical powder having a particle size that is less than a particle size of the asymmetric powder particles.

10. A method for increasing the surface roughness of a porous structure, comprising:
    machining a porous structure to a desired shape;
    bonding a powder to a machined tissue-interfacing outer surface of the machined porous structure, the powder comprising asymmetric powder particles; and
    applying one or more additional layers of powder to all surfaces of the porous structure, the one or more additional layers each comprising a fine spherical powder comprised of particles sized not greater than 45 micrometers, wherein the asymmetric powder particles are sized to increase the roughness of the machined tissue-interfacing outer surface of the machined porous structure while preventing the occlusion of the pores of the porous structure.

11. A method for increasing the surface roughness of a porous structure having a machined tissue-interfacing outer surface and one or more additional surfaces, comprising:
applying to the machined tissue-interfacing outer surface a plurality of powder particles having a particle size for maintaining a pore size of the machined tissue-interfacing outer surface;
bonding the plurality of powder particles to at least a portion of the machined tissue-interfacing outer surface of the machined porous structure;
maintaining, upon bonding of the plurality of powder particles, approximately the pore size of the machined tissue-interfacing outer surface,
wherein at least a portion of the plurality of powder particles has sufficient dimensions to increase the roughness of the machined tissue-interfacing outer surface of the machined porous structure without occluding a plurality of pores of the porous structure.

12. The method of claim 11, wherein at least a portion of the plurality of powder particles comprises asymmetric powder particles.

13. The method of claim 11, wherein the size of at least a portion of the plurality of powder particles is from about 75 micrometers to about 106 micrometers.

14. The method of claim 11, wherein said applying step includes applying a binder to the machined tissue-facing outer surface of the machined porous structure, and subsequently applying a quantity of the plurality of powder particles by one or more of dipping, spraying and sprinkling, and wherein said bonding step includes sintering the porous structure to bond a portion of the quantity of the plurality of powder particles to at least a portion of the machined tissue-facing outer surface of the porous structure.

15. The method of claim 11, wherein the porous structure comprises a metal foam structure.

16. The method of claim 11, further comprising the step of attaching the porous structure to a substrate.

17. The method of claim 16, wherein the substrate comprises a metallic foam-coated implant selected from the group consisting of a knee implant, hip implant, a shoulder implant, a spinal implant, a tibial tray, an acetabular shell, a femoral stem, and a stem collar.

18. The method of claim 11, further comprising applying one or more additional layers of the powder particles to the one or more additional surfaces of the porous structure.

19. The method of claim 18, wherein the step of applying the one or more additional layers occurs after the step of bonding the plurality of powder particles to the machined tissue-interfacing outer surface of the machined porous structure.

20. The method of claim 18, wherein at least one layer of the one or more additional layers comprises a plurality of fine spherical particles, wherein at least a portion of the fine spherical particles has a size of less than about 45 micrometers, the fine spherical particles having a particle size that is less than the particle size of the plurality of powder particles.

* * * * *